United States Patent
Perschbacher et al.

(10) Patent No.: US 11,832,968 B2
(45) Date of Patent: Dec. 5, 2023

(54) CONFIDENCE OF ARRHYTHMIA DETECTION

(71) Applicant: Cardiac Pacemakers, Inc., St. Paul, MN (US)

(72) Inventors: David L. Perschbacher, Coon Rapids, MN (US); Deepa Mahajan, Roseville, MN (US); Krzysztof Z. Siejko, Maple Grove, MN (US); Keith L Herrmann, Minneapolis, MN (US); Jonathan Walter Krueger, New Richmond, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 70 days.

(21) Appl. No.: 15/478,652

(22) Filed: Apr. 4, 2017

(65) Prior Publication Data
US 2017/0290550 A1 Oct. 12, 2017

Related U.S. Application Data

(60) Provisional application No. 62/319,055, filed on Apr. 6, 2016.

(51) Int. Cl.
*A61B 5/02* (2006.01)
*A61B 5/00* (2006.01)
(Continued)

(52) U.S. Cl.
CPC ........ *A61B 5/7221* (2013.01); *A61B 5/02405* (2013.01); *A61B 5/076* (2013.01);
(Continued)

(58) Field of Classification Search
CPC ... A61B 5/7275; A61B 5/7282; A61B 5/0452; A61B 5/0402; A61B 5/7264;
(Continued)

(56) References Cited

U.S. PATENT DOCUMENTS

| | | | |
|---|---|---|---|
| 5,817,135 | A | 10/1998 | Cooper et al. |
| 7,031,765 | B2 | 4/2006 | Ritscher et al. |

(Continued)

FOREIGN PATENT DOCUMENTS

| | | |
|---|---|---|
| AU | 2017246369 B2 | 7/2019 |
| CN | 108883279 A | 11/2018 |

(Continued)

OTHER PUBLICATIONS

Cowie, Martin R., et al., "Development and validation of an integrated diagnostic algorithm derived from parameters monitored in implantable devices for identifying patients at risk for heart failure in an ambulatory setting", European Heart Journal, [Online]. Retrieved from the Internet: <URL: [Online]. Retrieved from the Internet: <URL: http://eurheartj.oxfordjournals.org/, (Mar. 19, 2013), 9 pgs.

(Continued)

*Primary Examiner* — Deborah L Malamud
(74) *Attorney, Agent, or Firm* — Schwegman Lundberg & Woessner, P.A.

(57) ABSTRACT

Systems and methods for detecting an arrhythmic event and storing physiological information associated with the detected arrhythmic event are described. A system may include a first detector to detect an arrhythmic event from a physiological signal sensed from a subject, and generate a confidence indicator indicating a confidence level of the detection of the arrhythmic event. If the confidence indicator indicates a relatively high confidence of arrhythmia detection, the system may provide the detected arrhythmic event to a first process for storing the detected arrhythmic event or generating an alert. If the confidence indicator indicates a relatively low confidence of arrhythmia detection, the system may provide the detected arrhythmic event to at least a (Continued)

second process including confirming or rejecting the detected arrhythmic event.

20 Claims, 4 Drawing Sheets

(51) Int. Cl.
  *A61N 1/362* (2006.01)
  *A61N 1/37* (2006.01)
  *A61B 5/361* (2021.01)
  *A61B 5/364* (2021.01)
  *A61B 5/024* (2006.01)
  *A61B 5/07* (2006.01)

(52) U.S. Cl.
  CPC .............. *A61B 5/361* (2021.01); *A61B 5/364* (2021.01); *A61B 5/4836* (2013.01); *A61B 5/686* (2013.01); *A61B 5/7203* (2013.01); *A61B 5/746* (2013.01); *A61N 1/3621* (2013.01); *A61N 1/3627* (2013.01); *A61N 1/3704* (2013.01)

(58) Field of Classification Search
  CPC . A61B 5/0245; A61B 5/04012; A61B 5/0006; A61B 5/7246; A61B 5/00; A61B 5/486; A61B 5/72; A61B 5/7271; G06F 19/34; A61N 1/365; A61N 1/36135; A61N 1/3702; A61N 1/08; A61N 1/36125; A61N 1/37; G06K 9/00496; G06K 9/00523
  See application file for complete search history.

(56) References Cited

U.S. PATENT DOCUMENTS

| | | | | |
|---|---|---|---|---|
| 7,713,213 B2* | 5/2010 | Siejko | ............... | A61B 5/00 600/508 |
| 8,700,140 B2* | 4/2014 | Narayan | ............... | A61B 5/0255 600/518 |
| 8,744,560 B2* | 6/2014 | Gunderson | ........ | A61N 1/37247 600/518 |
| 8,781,566 B2* | 7/2014 | John | ............... | A61B 5/0452 600/509 |
| 2004/0215273 A1 | 10/2004 | Van Bolhuis et al. | | |
| 2007/0213599 A1 | 9/2007 | Siejko et al. | | |
| 2012/0203123 A1 | 8/2012 | Mahajan et al. | | |
| 2013/0225263 A1 | 8/2013 | Thompson et al. | | |
| 2013/0274624 A1 | 10/2013 | Mahajan et al. | | |
| 2014/0257421 A1 | 9/2014 | Sanghera et al. | | |
| 2015/0157273 A1 | 6/2015 | An et al. | | |
| 2015/0297907 A1 | 10/2015 | Zhang | | |
| 2015/0327776 A1 | 11/2015 | Zhang et al. | | |
| 2016/0220139 A1 | 8/2016 | Mahajan et al. | | |
| 2016/0287115 A1 | 10/2016 | Perschbacher et al. | | |

FOREIGN PATENT DOCUMENTS

| | | |
|---|---|---|
| CN | 108883279 B | 5/2022 |
| EP | 3439737 B1 | 1/2020 |
| JP | 2011509706 A | 3/2011 |
| JP | 2011528933 A | 12/2011 |
| JP | 2019510584 A | 4/2019 |
| JP | 2021184963 A | 12/2021 |
| WO | WO-2017176714 A1 | 10/2017 |

OTHER PUBLICATIONS

Lynn, K. S., et al., "A Two-stage Solution Algorithm for Paroxysmal Atrial Fibrillation Prediction", Computers in Cardiology, 28, (2001), 405-407.

Purerfeliner, Helmut, et al., "P-wave evidence as a method for improving algorithm to detect atrial fibrillation in insertable cardiac monitors", (2014), 1575-1583.

Whellan, David J., et al., "Combined Heart Failure Device Diagnostics Identify Patiens at Higher Risk of Subsequent Heart Failure Hospitalizations", Journal of the American College of Cardiology, vol. 55, No. 17, (2010), 1803-1810.

"Australian Application Serial No. 2017246369, First Examination Report dated Feb. 17, 2019", 3 pgs.

"Australian Application Serial No. 2017246369, Response Filed Jun. 7, 2019 to First Examination Report dated Feb. 17, 2019", 13 pgs.

"European Application Serial No. 17718661.6, Response Filed May 29, 2019 to Communication pursuant to Rules 161(2) and 162 EPC dated Nov. 22, 2018", 15 pgs.

"International Application Serial No. PCT/US2017/025894, International Preliminary Report on Patentability dated Oct. 18, 2018", 7 pgs.

"International Application Serial No. PCT/US2017/025894, International Search Report dated Jul. 13, 2017", 4 pgs.

"International Application Serial No. PCT/US2017/025894, Written Opinion dated Jul. 13, 2017", 7 pgs.

"Japanese Application Serial No. 2018-552747, Notification of Reasons for Refusal dated Oct. 1, 2019", W/ English Translation, 12 pgs.

"Japanese Application Serial No. 2018-552747, Response filed Feb. 26, 2020 to Notification of Reasons for Refusal dated Oct. 1, 2019", w/ English claims, 10 pgs.

"Japanese Application Serial No. 2018-552747, Notification of Reasons for Refusal dated Jul. 14, 2020", w/ English translation, 5 pgs.

"Japanese Application Serial No. 2018-552747, Response filed Dec. 14, 2020 to Notification of Reasons for Refusal dated Jul. 14, 2020", w/ English claims, 10 pgs.

"Chinese Application Serial No. 201780022402.3, Office Action dated Aug. 12, 2021", (w/ English Translation), 17 pgs.

"Japanese Application Serial No. 2018-552747, Examiners Decision of Final Refusal dated May 18, 2021", (w/ English Translation), 8 pgs.

"Chinese Application Serial No. 201780022402.3, Response filed Dec. 7, 2021 to Office Action dated Aug. 12, 2021", w/ English Claims, 13 pgs.

"Japanese Application Serial No. 2018-552747, Preliminary Examination Report dated Jul. 12, 2022", w/ English Translation, 6 pgs.

* cited by examiner

CONFIDENCE OF ARRHYTHMIA DETECTION

CLAIM OF PRIORITY

This application claims the benefit of priority under 35 U.S.C. § 119(e) of U.S. Provisional Patent Application Ser. No. 62/319,055, filed on Apr. 6, 2016, which is herein incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

The IMDs may be programmed to store physiological data in a memory. The physiological data may be retrieved and presented to a system user such as a clinician in a display device. The system user may review the stored physiological data to determine the presence or causes of a physiological event, or to determine whether a device therapy results in desired therapeutic outcome.

Some IMDs are able to detect cardiac arrhythmias, such as atrial fibrillation (AF). AF is the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself, persistent that may last for over a week and typically requires medication or other treatment to revert to normal sinus rhythm, or permanent where a normal heart rhythm cannot be restored with treatment. Timely detection of AF, and storing electrograms and other physiological information associated with the AF, may be clinically important for assessing progression of AF.

OVERVIEW

Implantable medical devices are capable of detecting physiological events, such as cardiac arrhythmias or progression of chronic heart diseases, and obtaining sampled values of cardiac electrical activity signals such as electrograms. Some IMDs may further be communicated with multiple physiological sensors that may measure various physiological signals. The IMD may be programmed to monitor and store data sensed from some or all of the physiological sensors.

Capturing accurate electrogram or other physiological sensor information obtained over a longer period of time, such as chronically between regularly-scheduled outpatient office visits, may help the physician re-program the device, if needed, or to diagnose and assess the patient's condition. Recording of electrograms or other physiological sensor data may be limited by the restricted data storage space available within the IMD. In an IMD programmed to detect cardiac arrhythmias such as atrial fibrillation (AF) events, noise, motion artifacts, or cardiac rhythms other than the AF event may be inappropriately detected as AF events. Inappropriate arrhythmia detection may reduce detection specificity and result in inappropriate treatment to patients. Additionally, storing the inappropriately detected arrhythmic events may waste and quickly exhaust device memory. Alerts to clinicians of inappropriately detected arrhythmic events, or presenting to clinicians a large volume of inappropriately detected arrhythmic events for review or adjudication, may adversely affect the device efficacy and unwarrantedly increase the cost associated with patient management. For at least these reasons, the present inventors have recognized, among other things, substantial challenges and a demand for a more efficient arrhythmic detection and reporting system, while storing the most relevant arrhythmic events or presenting these events to a clinician.

This document discusses, among other things, systems, devices, and methods for detecting an arrhythmic event and storing physiological information associated with the detected arrhythmic event. A system may include a first detector to detect an arrhythmic event from a physiological signal sensed from a subject, and generate a confidence indicator indicating a confidence level of the detection of the arrhythmic event. If the confidence indicator indicates a relatively high confidence of arrhythmia detection, the system may provide the detected arrhythmic event to a first process for storing the detected arrhythmic event or generating an alert. If the confidence indicator indicates a relatively low confidence of arrhythmia detection, the system may provide the detected arrhythmic event to at least a second process including confirming the detected arrhythmic event.

In Example 1, a system may include a physiological sensor circuit to sense a physiological signal from a subject, a first arrhythmia detector circuit configured to detect an arrhythmic event from the sensed physiological signal, a confidence indicator generator circuit configured to generate a confidence indicator for the detected arrhythmic event, the confidence indicator indicating a confidence level of the detection of the arrhythmic event, and a controller circuit coupled to the arrhythmia detector circuit and configured to provide the detected arrhythmic event to a first process in response to the confidence indicator indicating a first confidence level, and provide the detected arrhythmic event to at least a second process different from the first process in response to the confidence indicator indicating a different second confidence level.

Example 2 may include, or may optionally be combined with the subject matter of Example 1 to optionally include, the first arrhythmia detector circuit that may detect the arrhythmic event including an atrial or ventricular arrhythmia.

Example 3 may include, or may optionally be combined with the subject matter of one or any combination of Examples 1 or 2 to include, the controller circuit that may be configured to provide the detected arrhythmic event to the first process in response to the confidence indicator exceeding a confidence threshold indicative of a high confidence of the detection of the arrhythmic event. The first process may include storing the detected arrhythmic event in a memory circuit, or producing an alert signal.

Example 4 may include, or may optionally be combined with the subject matter of one or any combination of Examples 1 through 3 to include, the controller circuit that may, provide the detected arrhythmic event to the at least second process in response to the confidence indicator falling below a confidence threshold indicative of a low confidence of the detection of the arrhythmic event. The second process may include detecting the arrhythmic event using at least a second arrhythmia detector circuit to confirm the detected arrhythmic event. The second arrhythmia detector circuit may have more computational power or execute a more computationally intensive algorithm than the first arrhythmia detector.

Example 5 may include, or may optionally be combined with the subject matter of one or any combination of Examples 1 through 4 to include, the physiological sensor circuit that may receive the physiological signal including a cardiac signal, and the first arrhythmia detector circuit that may include a filter circuit to generate a signal metric from the cardiac signal, the first arrhythmia detector circuit configured to detect the arrhythmic event in response to the signal metric satisfying a specified condition.

Example 6 may include, or may optionally be combined with the subject matter of Example 5 to optionally include, the signal metric that may include a first number of stable beats from the cardiac signal within a specified time period, a second number of unstable beats from the cardiac signal within the specified time period, or a third number of a relative number between the first and second numbers.

Example 7 may include, or may optionally be combined with the subject matter of Example 5 to optionally include, the signal metric that may include a heart rate distribution of a plurality of heart rate measurements from the cardiac signal. The rate distribution may include a central tendency of the heart rate measurements, or a relative number of the heart beats falling within a specified margin of the central tendency of the heart rate measurements.

Example 8 may include, or may optionally be combined with the subject matter of Example 5 to optionally include, the signal metric that may include morphology measurements of a plurality of heart beats from the cardiac signal. The first arrhythmia detector circuit may detect the arrhythmic event using the morphology measurements of the plurality of heart beats.

Example 9 may include, or may optionally be combined with the subject matter of one or any combination of Examples 5 through 8 to include, the confidence indicator generator circuit that may determine for the detected arrhythmic event the confidence indicator including a confidence score proportional to a deviation of the signal metric from a reference value.

Example 10 may include, or may optionally be combined with the subject matter of Example 9 to optionally include, the confidence indicator generator circuit that may determine the confidence score using a combination of deviations of two or more signal metrics from respective reference values.

Example 11 may include, or may optionally be combined with the subject matter of one or any combination of Examples 5 through 10 to include, the confidence indicator generator circuit that may determine the confidence indicator based on a signal quality of the signal metric. The signal quality may include one of a signal-to-noise ratio, a detection of motion artifact, or a detection of ectopic beats.

Example 12 may include, or may optionally be combined with the subject matter of one or any combination of Examples 5 through 11 to include, the confidence indicator generator circuit that may determine the confidence indicator based on a medical history of the subject including one of a history of syncope, an arrhythmia history, an ablation procedure, or a duration of a prior arrhythmic event.

Example 13 may include, or may optionally be combined with the subject matter of one or any combination of Examples 1 through 12 to include, an output circuit that may be configured to generate a human-perceptible presentation of the detected arrhythmic events.

Example 14 may include, or may optionally be combined with the subject matter of Example 13 to optionally include, a prioritizer circuit that may include a comparator circuit to prioritize two or more detected arrhythmic events based on the respective confidence indicators. The output circuit may generate the presentation including at least a portion of the prioritized two or more detected arrhythmic events.

Example 15 may include, or may optionally be combined with the subject matter of Example 4 to optionally include, a first implantable device that may include the first arrhythmia detector circuit and a different second device including the second arrhythmia detector circuit.

In Example 16, a method for detecting an arrhythmic event via a medical system is disclosed. The method may include steps of: sensing a physiological signal from a subject; detecting, via a first arrhythmia detector, an arrhythmic event from the sensed physiological signal; generating a confidence indicator for the detected arrhythmic event, the confidence indicator indicating a confidence level of the detection of the arrhythmic event; and providing the detected arrhythmic event to a first process in response to the confidence indicator indicating a first confidence level, or providing the detected arrhythmic event to at least a second process different from the first process in response to the confidence indicator indicating a different second confidence level.

Example 17 may include, or may optionally be combined with the subject matter of Example 16 to optionally include, a method of generating one or more signal metrics from a cardiac signal. The detection of the arrhythmic event may include detecting an atrial or ventricular arrhythmia using the one or more signal metrics.

Example 18 may include, or may optionally be combined with the subject matter of Example 17 to optionally include, the one or more signal metrics that may include morphology measurements of a plurality of heart beats from the cardiac signal, and the detection of the arrhythmic event may be based on the morphology measurements of the plurality of heart beats.

Example 19 may include, or may optionally be combined with the subject matter of Example 16 to optionally include, a step of providing the detected arrhythmic event to the first process that may include, in response to the confidence indicator exceeding a confidence threshold indicative of a high confidence of the detection of the arrhythmic event, storing the detected arrhythmic event in a memory circuit or producing an alert signal.

Example 20 may include, or may optionally be combined with the subject matter of Example 16 to optionally include, the method of providing the detected arrhythmic event to the at least second process that may include, in response to the confidence indicator falling below a confidence threshold indicative of a low confidence of the detection of the arrhythmic event, confirming the detected arrhythmic event via at least a second arrhythmia detector having more computational power or executing computationally intensive algorithm than the first arrhythmia detector.

Example 21 may include, or may optionally be combined with the subject matter of Example 16 to optionally include, the confidence indicator that may include a confidence score proportional to deviations of the one or more signal metrics from respective reference values.

Example 22 may include, or may optionally be combined with the subject matter of Example 16 to optionally include, the confidence indicator that may be generated based on one of a signal quality of the signal metric or a medical history of the subject. The signal quality may include one of a signal-to-noise ratio, a detection of motion artifact, or a detection of ectopic beats, and the medical history may include one of a history of syncope, an arrhythmia history, an ablation procedure, or a duration of a prior arrhythmic event.

Example 23 may include, or may optionally be combined with the subject matter of Example 16 to optionally include, steps of prioritizing two or more detected arrhythmic events based on the respective confidence indicators, generating a presentation of at least a portion of the prioritized two or more detected arrhythmic events, and receiving from a user, via the user interface, adjudication of at least a portion of the prioritized two or more detected arrhythmic events.

The systems, devices, and methods discussed in this document may improve the medical technology of automated cardiac rhythm management (CRM) and prevention of worsening of cardiac function. The confidence-based arrhythmia detection using first and second detection processes may also enhance the performance and functionality of an implantable CRM device, in certain examples, increasing the specificity of existing arrhythmia detection (e.g., reducing false positives), such that system performance can be improved with little to no additional cost, while reducing costs associated with false detections, or manual inspection required by such false determinations. The present arrhythmia detection also allows for more efficient use of device memory, such as by storing heart rate statistics that are clinically relevant to arrhythmia recognition, and a smaller number of potential arrhythmia events. As fewer alarms are provided, battery life can be extended, fewer unnecessary drugs and procedures may be scheduled, prescribed, or provided, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting a target physiologic event and storing physiologic information associated with the target physiologic event. The target physiologic event, such as an atrial fibrillation (AF) episode, can be detected from a physiological signal using a first detector. A confidence indicator indicating a confidence level of the detection of the arrhythmic event may be generated. The system may provide the detected arrhythmic event to a first process if the confidence indicator indicating a first confidence level, and to provide the detected arrhythmic event to at least a second process if the confidence indicator indicating a different second confidence level.

Figure 1:
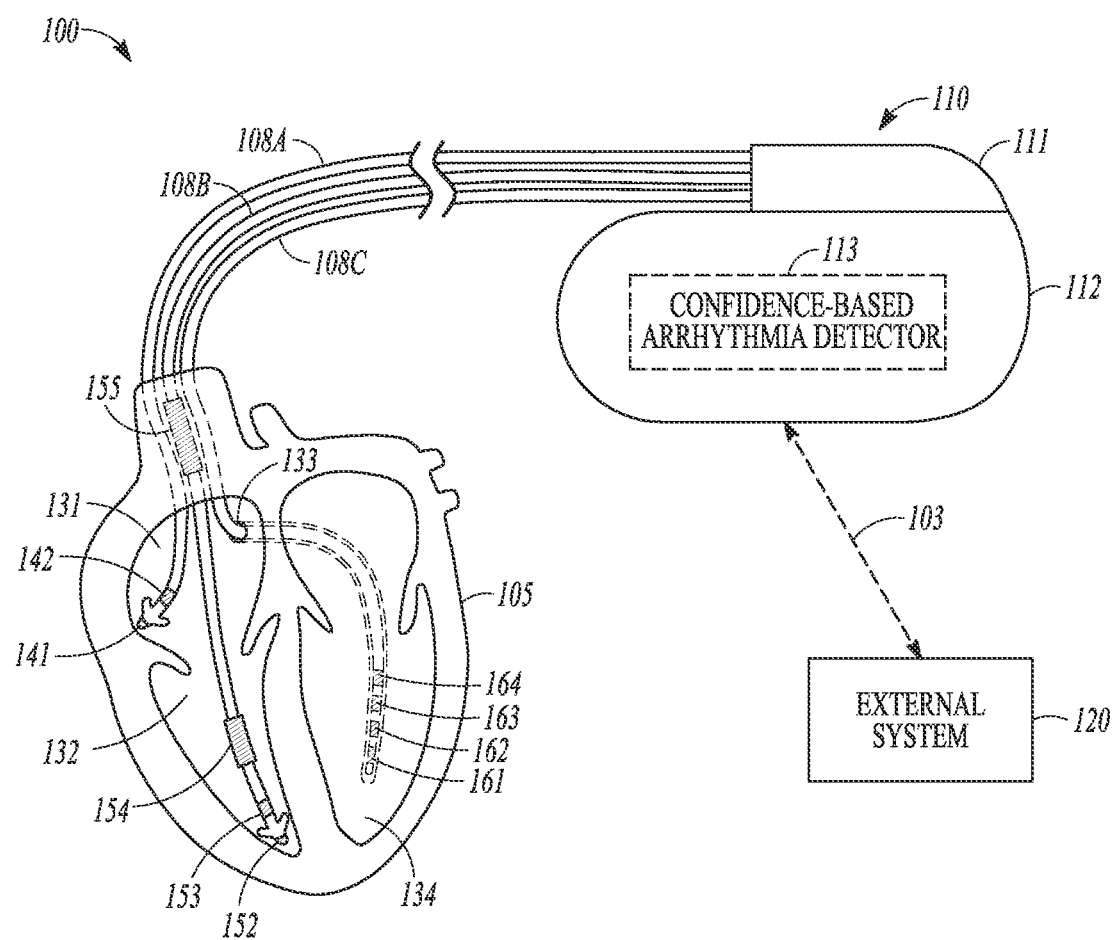
FIG. 1 illustrates an example of a Cardiac Rhythm Management (CRM) system and portions of an environment in which the CRM system may operate.

FIG. 1 illustrates generally an example of a Cardiac Rhythm Management (CRM) system 100 and portions of an environment in which the CRM system 100 may operate. The CRM system 100 may include an ambulatory medical device, such as an implantable medical device (IMD) 110 that may be electrically coupled to a heart 105 such as through one or more leads 108A-C, and an external system 120 that may communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). In some examples, the CRM system may include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

The IMD 110 may include a hermetically sealed can housing 112 that may house an electronic circuit that may sense a physiological signal in the heart 105 and may deliver one or more therapeutic electrical pulses to a target region, such as in the heart, such as through one or more leads 108A-C. The CRM system 100 may include only one lead such as 108B, or may include two leads such as 108A and 108B.

The lead 108A may include a proximal end that may be configured to be connected to IMD 110 and a distal end that may be configured to be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMD 110 such as via separate conductors in the lead 108A, such as to allow for sensing of the right atrial activity and optional delivery of atrial pacing pulses. The lead 108B may be a defibrillation lead that may include a proximal end that may be connected to IMD 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular electrogram and may allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMD 110 and a distal end that may be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161. The electrodes 161 and 162 may be electrically connected to the IMD 110 such as via separate conductors in the lead 108C such as to allow for sensing of the LV electrogram and allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMD 110 may include an electronic circuit that may sense a physiological signal. The physiological signal may include an electrogram or a signal representing mechanical function of the heart 105. The hermetically sealed can housing 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 may sense impedance such as between electrodes located on one or more of the leads 108A-C or the can housing 112. The IMD 110 may be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing.

In an example, the IMD 110 may be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMD 110. The IMD 110 may also be configured to sense a physiological signal from one or more external physiological sensors or one or more external electrodes that may be coupled to the IMD 110. Examples of the physiological signal may include one or more of thoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of non-limiting example and not by way of limitation. Depending on the need of the patient and the capability of the implantable device, other arrangements and uses of these leads and electrodes are contemplated.

As illustrated, the CRM system 100 may include a confidence-based arrhythmia detector 113 for detecting an arrhythmia, such as an atrial fibrillation (AF) event. The confidence-based arrhythmia detector 113 may generate a confidence indicator that indicates a confidence level of the detected arrhythmia. The detection of the arrhythmia and determination of the confidence score may be based on one or more signal metrics derived from a physiological signal. If the confidence indicator indicates a high confidence of arrhythmia being detected, the detected arrhythmic event may be provided to a first process, such as for storing the detected arrhythmia to a memory or generating an alert to a healthcare professional. If the confidence indicator indicates a low confidence associated with the detected arrhythmia, the detected arrhythmic event may be provided to at least a second process different from the first process, such as configuring a secondary arrhythmia detector with more computational power or resources to confirm the detected arrhythmic event, or configuring an arrhythmia adjudicator to receive arrhythmia adjudication from a clinician. Examples of the confidence-based arrhythmia detector 113 are described below, such as with reference to FIGS. 2-4.

The external system 120 may allow for programming of the IMD 110 and may receive information about one or more signals acquired by IMD 110, such as may be received via a communication link 103. The external system 120 may include a local external IMD programmer. The external system 120 may include a remote patient management system that may monitor patient status or adjust one or more therapies such as from a remote location.

The communication link 103 may include one or more of an inductive telemetry link, a radio-frequency telemetry link, or a telecommunication link, such as an internet connection. The communication link 103 may provide for data transmission between the IMD 110 and the external system 120. The transmitted data may include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that may include physiological data acquisition such as using programmably specifiable sensing electrodes and configuration, device self-diagnostic test, or delivery of one or more therapies.

The confidence-based arrhythmia detector 113, although illustrated in FIG. 1 as being implemented in the IMD 110, may alternatively be implemented in a subcutaneously implanted device, a wearable external device, a neural stimulator, a drug delivery device, a biological therapy device, or one or more diagnostic devices. In some examples, the confidence-based arrhythmia detector 113 may be implemented in the external system 120. The external system 120 may be configured to perform worsening heart failure (WHF) event detection such as using data extracted from the IMD 110 or data stored in a memory within the external system 120. The external system 120 may include a user interface that may display information about detection of the target physiological events, including onset and resets thresholds. In an example, portions of the confidence-based arrhythmia detector 113 may be distributed between the IMD 110 and the external system 120.

Portions of the IMD 110 or the external system 120 may be implemented using hardware, software, or any combination of hardware and software. Portions of the IMD 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
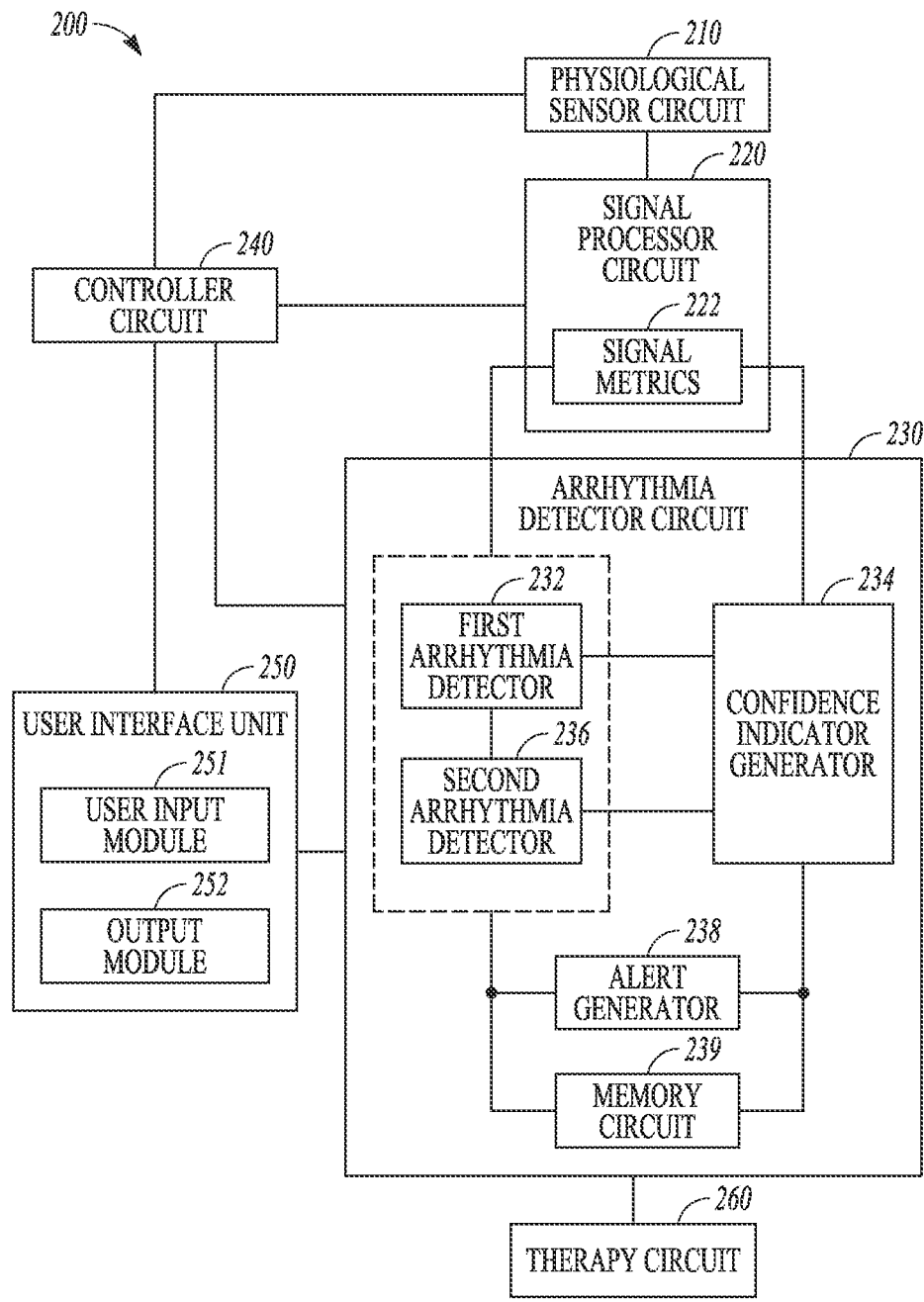
FIG. 2 illustrates generally an example of an arrhythmia detection system configured to detect a target cardiac arrhythmia from a patient.

FIG. 2 illustrates generally an example of an arrhythmia detection system 200 that may be configured to detect a target cardiac arrhythmia from a patient, such as an atrial fibrillation (AF) event. The arrhythmia detection system 200 may be an embodiment of the confidence-based arrhythmia detector 113. The arrhythmia detection system 200 may include one or more of a physiological sensor circuit 210, a signal processor circuit 220, an arrhythmia detector circuit 230, a controller circuit 240, and a user interface unit 250.

The physiological sensor circuit 210 may include a sense amplifier circuit to sense a physiological signal sensed from a patient. The physiological signals may be indicative or correlative of a disease state or a physical or physiological condition. The physiological signals may be sensed using one or more implantable, wearable, or otherwise ambulatory sensors associated with the patient. Examples of the physiological signals may include surface electrocardiography (ECG) such as sensed from electrodes on the body surface, subcutaneous ECG such as sensed from electrodes placed under the skin, intracardiac electrogram (EGM) sensed from the one or more electrodes of the leads 108A-C or the can housing 112, heart rate signal, heart rate variability signal, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The physiological sensor circuit 210 may include one or more other sub-circuits to digitize, filter, or perform other signal conditioning operations on the received physiological signal.

In an example, the signal physiological sensor circuit 210 may retrieve from an electronic medical record (EMR) system one or more patient historical physiological signals in response to a command signal. The command signal may be issued by a system user (e.g., a health-care professional) such as via an input device coupled to the instruction receiver 250, or generated automatically by the system in response to a specified event. The signal physiological sensor circuit 210 may include one or more sub-circuits that may perform signal conditioning or pre-processing, including signal amplification, digitization, or filtering, on the one or more physiological signals.

The signal processor circuit 220, coupled to the physiological sensor circuit 210, may include a filter circuit to filter the sensed physiological signal to generate one or more signal metrics 222. In an example, the signal processor circuit 220 includes a beats detector for detecting pulsatile activity of the heart, hereinafter referred to as "beats", from the sensed physiological signal. The beats may be detected from a cardiac electrical signal such as a surface electrocardiograph (ECG), a subcutaneous ECG, or an intracardiac electrogram (EGM). The beats may additionally or alternatively be detected from a cardiac mechanical signal indicative of pulsatile contraction of the heart, including a cardiac impedance signal, a heart sounds signal, or a blood pressure signal, among others. The cardiac mechanical signals may vary within a cardiac cycle, and exhibit a pulsatile pattern consistent with the periodic cardiac electrical activities. Beat detection may include detection of a EGC signal component such as a P wave, an R wave, a T wave, or a QRS complex, localized myocardial depolarization or repolarization sensed from a EGM signal, or peak or trough amplitude, peak value of an envelope or an integral, or other intensity measures of a cardiac impedance signal, a heart sound signal, or a blood pressure signal.

The signal metrics 222 may include timing parameters associated with the beats detected from the sensed physiological signal. Examples of the timing parameters may include cardiac intervals (CI) or heart rates (HR) signal, electro-mechanical delay such as a systolic timing interval (STI) such as measured between the onset of the QRS complex on the ECG or the atrial activation event in an intracardiac EGM and the S2 heart sound, a pre-ejection period (PEP) such as measured between the onset of the QRS and the S1 heart sound, a diastolic timing interval (DTI) such as measured between the S2 heart sound and the onset of the QRS complex on the ECG or the atrial activation event in an intracardiac EGM of the next cardiac cycle. Additionally or alternatively, the signal metrics 222 may include statistical or morphological parameters associated with the detected beats from the sensed physiological signal. Examples of the statistical or morphological parameters may include signal maximum or minimum within a specified time period such as a cardiac cycle, positive or negative slope or higher order statistics, or a signal power spectral density at a specified frequency range, among others. Depending on the types of the sensed physiological signal, examples of the signal metrics may include thoracic impedance magnitude, S3 heart sound intensity, a ratio of S3 heart sound intensity to a reference heart sound intensity (such as S1 heart sound intensity, heart sound signal energy between R-wave and S2, or heart sound signal energy within a cardiac cycle), a respiration rate, a tidal volume, a ratio a respiration rate to a tidal volume, an activity intensity, or a time duration when the activity intensity is within a specified range or above a specified threshold, among others.

The arrhythmia detector circuit 230 may be configured to use at least the signal metrics 222 to detect a target cardiac arrhythmic event and to determine a confidence indicator for the detected arrhythmic event. Examples of cardiac arrhythmias may include atrial fibrillation (AF), atrial flutter (AFL), atrial tachycardia, paroxysmal supraventricular tachycardia (PSVT), Wolff-Parkinson-White (WPW) syndrome, ventricular tachycardia, ventricular fibrillation, bradycardia, or sinus pauses, among others.

The arrhythmia detector circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the physiological sensor circuit 210. Alternatively, the microprocessor circuit may be a general purpose processor that may receive and execute a set of instructions of performing the functions, methods, or techniques described herein.

The arrhythmia detector circuit 230 may include circuit sets comprising one or more other circuits or sub-circuits, such as one or more of a first arrhythmia detector 232, a confidence indicator generator 234, at least a second arrhythmia detector 236, an alert generator circuit 238, and a memory circuit 239. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The first arrhythmia detector circuit 232 may be configured to generate an initial detection of an arrhythmic event using the signal metrics 222 of the sensed physiological signal. In an example, based on the variability of the CI or HR associated with the detected beats, the detected heart beats may be classified into one of a plurality of beat classes including a stable beat class, an unstable beat class, and a random beat class. The first arrhythmia detector 232 may determine beat counts (i.e., number of beats within a specified time period) of the stable beats, unstable beats, or random beats, and generate a relative quantity, such as a difference, a ratio, a proportion, or a percentage, using the beat counts of the beat classes. Examples of the relative quantity may include a ratio of the number of unstable beats to a sum of the numbers of the stable and unstable beats, or a ratio of the number of random beats to a sum of the numbers of the stable and unstable beats. The first arrhythmia detector 232 may detect the target cardiac arrhythmic event, such as an AF event, in response to the relative quantity satisfying a specified condition, such as those disclosed in the commonly assigned Mahajan et al. U.S. Provisional Patent Application Ser. No. 62/109,963, entitled "PHYSIOLOGIC EVENT DETECTION AND DATA STORAGE," filed on Jan. 30, 2015, which is hereby incorporated by reference in its entirety, including its disclosure of beats classes and AF detection using at least the beat classes.

A heart rate distribution may be generated from a plurality of heart beats from the cardiac signal within a specified time period, and the signal metric may include a parameter extracted from the heart rate distribution. In an example, the distribution parameter may include a central tendency of heart rates within the specified time period. Examples of the central tendency may include a mean, a median, or a mode, among others. In another example, the distribution parameter may include a relative number of the heart beats falling within a specified margin of the central tendency of the heart rates.

The heart rate distribution may be represented by a heart rate histogram that includes percentages of the heart beats during a specified time period that fall within each of a plurality of heart rate bins. Each heart rate bin defines a range of heart rates. The indicator may include a mode of the heart rates, such as a histogram bin (or a representative heart rate value of that histogram bin) that includes the most heart beats with corresponding heart rates falling within that histogram bin. The indicator may alternatively or additionally include a heart rate density index (HRDI), which may be calculated as a percentage of the heart beats falling within the histogram bin including the mode of the heart rates. The first arrhythmia detector 232 may detect the target cardiac arrhythmia such as an AF event in response to the mode of the heart rate or the HRDI each satisfies a specified condition, such as those disclosed in the commonly assigned Mahajan et al. U.S. Provisional Patent Application Ser. No. 62/142,184, entitled "ATRIAL FIBRILLATION DETECTION," filed Apr. 2, 2015, which is hereby incorporated by reference in its entirety, including its disclosure of the HRDI and the AF detection using at least the HRDI.

In various examples, the signal metric may include morphology measurements of a plurality of heart beats from a cardiac electrical or mechanical signal. The morphology measurements may include a plurality of morphological features such as samples selected from a portion of a waveform of the signal metric within a beat (or a cardiac cycle). In an example, the morphological features may include characteristic points of the waveform such as a peak, a trough, an inflection point, or one or more intermediate points between the characteristic points. The first arrhythmia detector 232 may receive from a user such as via the user interface unit 250, or retrieve from a memory device, a template that represents the morphology of the same signal metric that is obtained during a known rhythm such as a sinus rhythm or a specified arrhythmia such as AF. The first arrhythmia detector 232 may compare the morphology measurements of the plurality of beats to the template, and compute a similarity score between the morphology measurements and template. Examples of the similarity score may include a correlation, a sum of differences between the morphology measurements and scaled template, or a distance measure in a multi-dimensional signal feature space. In an example, the arrhythmia detector 232 may dynamically update the template using the morphology measurements of previous one or more beats that are morphologically similar to the received or retrieved template (such as the similarity score falling within a specified range). The first arrhythmia detector 232 may detect the cardiac arrhythmia in response to the similarity score satisfying a specified condition, such as when the difference falls below a specified detection threshold.

The confidence indicator generator 234 may generate for the detected arrhythmic event a confidence indicator indicating a confidence level of the detection of the arrhythmic event. The confidence indicator may include a categorical descriptor such as a "high", "medium", or "low" confidence, or a numerical confidence score within a specified range, where a higher score indicates a higher confidence about the presence of the cardiac arrhythmic event. In an example as illustrated in FIG. 2, the confidence indicator generator 234 may be coupled to the signal processor circuit 220, and to generate the confidence indicator based on a comparison of the signal metrics 222 and one or more thresholds. In an example, the same signal metrics used by the first arrhythmia detector 232 for detecting the cardiac arrhythmic event may be used for generating the confidence indicator. In an example, at least one signal metric for generating the confidence indicator may be different from the signal metrics for detecting the cardiac arrhythmic event by the first arrhythmia detector 232. Examples of the confidence indicator generator 234 are discussed below, such as with reference to FIG. 3.

The second arrhythmia detector 236 may be coupled to the first arrhythmia detector 232 and the confidence indicator generator 234, and configured to further detect the cardiac arrhythmic event when the confidence indicator associated with the first detection satisfies a specified condition, such as when a "low" confidence level is indicated or the numerical confidence score falls below a confidence threshold. In an example, the second arrhythmia detector 236 is to confirm the presence of arrhythmic event detected by the first arrhythmia detector 232. The second arrhythmia detector 236 may have more computational power than the first arrhythmia detector. In an example, the second arrhythmia detector 236 may detects cardiac arrhythmia using a computationally intensive algorithm, which may have a higher sensitivity or specificity or be configured to process larger amount of data for detecting the arrhythmic event than the first arrhythmia detector 232. Examples of the computationally intensive algorithm may include decision trees, neural networks, or support vector machine, among other linear or nonlinear pattern recognition methods. The computationally intensive algorithm may be implemented using circuits or sub-circuits, or a microprocessor that stores and executes a set of instructions such as for data processing. In an example, the second arrhythmia detector 236 may wait longer or use information in addition to the signal metrics 222 for detecting or confirming the cardiac arrhythmic event, such as additional data acquired by various physiological sensors. In an example, the second arrhythmia detector 236 may perform retrospective analysis of historical physiological data collected from the patient, as opposed to a real-time analysis such as used by the first arrhythmia detector. In some examples, additional arrhythmia detectors in addition to the second arrhythmia detector 236 may be included to further confirm or reject the presence of arrhythmic event.

Although the second arrhythmia detector 236 is shown as an example in FIG. 2 to be within the arrhythmia detector circuit 230, in some examples the second arrhythmia detector 236 may be implemented in a separate device than the first arrhythmia detector 232, such as in a programmer, a hand-held, wearable, or other portable device, or a server. In an example, portions of the sub-circuits in the arrhythmia detector circuit 230, such as the first arrhythmia detector 232 and the second arrhythmia detector 236, may be distributed between the IMD 110 and the external system 120.

The alert generator 238 may be coupled to the first arrhythmia detector 232 and the confidence indicator generator 234, and configured to generate an alert for presenting to a clinician when the confidence indicator associated with the first detection satisfies a specified condition, such as when a "high" confidence level is indicated or the numerical confidence score exceeds a detection threshold. Additionally or alternatively, the detected arrhythmic event may be stored in a memory circuit 239 if a high confidence level of the first detection of arrhythmic event is indicated. In an example, the amount of data stored may be based on the confidence level of the first detection to achieve more efficient memory usage. For example, if the confidence is indicated to be "very high", such as when the confidence score exceeds a confidence threshold higher than the detection threshold, a shorter episode of a detected AF event may be stored. If the confidence is indicated to be "marginally high", a longer duration of a detected AF event that covers at least a portion of physiological data prior to the detected onset of the AF event or following the detected AF event, or additionally together with other patient physiological information during the detected AF event, may be stored. By providing more relevant information to the clinician to assist arrhythmia adjudication in case of a marginal confidence about the automated arrhythmia detection, the confidence-based information storage described herein may provide more efficient use of the computing resources and storage space, or to allow the clinician to more efficiently identify and review or skip reviewing arrhythmias of marginal confidence.

The confidence indicator generator 234 may be coupled to the second arrhythmia detector 236, and to generate a confidence indicator associated with the second detection when the second arrhythmia detector 236 confirms the cardiac arrhythmic events. If the confidence level satisfies a specified condition, such as when a "high" confidence level is indicated or the numerical confidence score exceeds a confidence threshold, the alert generator 238 may generate an alert for presenting to a clinician. In an example, the alert may be accompanied by a report presenting to the clinician including the first and second arrhythmia detections. Also in response to the high confidence level of the second detection of arrhythmic event, the detected arrhythmic event as confirmed by the second arrhythmia detector 236 may be stored in a memory circuit 239.

The controller circuit 240 may control the operations of the physiological sensor circuit 210, the signal processor circuit 220, the arrhythmia detector circuit 230, the user interface unit 250, and the data and instruction flow between these components. The controller circuit 240 may control the first and second arrhythmia detectors and the operations based on the detection and at confidence associated with the detection. For example, the controller circuit 240 may provide the first arrhythmia detection by the first arrhythmia detector 232 to a first process in response to the confidence score indicating a first confidence level, such as storing the detected arrhythmia to a memory circuit or generating an alert to a clinician if the confidence indicator indicates a high confidence of arrhythmia being detected. The controller circuit 240 may provide the detected arrhythmic event, as detected by first arrhythmia detector 232, to at least a second process different from the first process in response to the confidence score indicating a different second confidence level, such as configuring a secondary arrhythmia detector to confirm the detected arrhythmic event, or configuring an arrhythmia adjudicator to receive arrhythmia adjudication from a clinician, if the confidence indicator indicates a low confidence associated with the detected arrhythmia.

The user interface unit 250 may include a user input module 251 and an output module 252. In an example, at least a portion of the user interface unit 250 may be implemented in the external system 120. The user input module 251 may receive a user's programming input, such as respective parameters for arrhythmia detection used by the first arrhythmia detector 232 and the second arrhythmia detector 236, or the thresholds for categorizing the confidence level into a high or low confidence levels, among others. The user input module 251 may include an input device such as a keyboard, on-screen keyboard, mouse, trackball, touchpad, touch-screen, or other pointing or navigating devices. The input device may enable a system user to program the parameters used for sensing the physiological signals, detecting the arrhythmias, and generating alerts, among others. The output module 252 may generate a human-perceptible presentation of information including one or more of the detection of the target cardiac arrhythmia, confidence indicators associated with the detected arrhythmic events, alerts generated for the detected arrhythmias, or other system information. The output module 252 may include a display for displaying the information. The information may be presented in a table, a chart, a diagram, or any other types of textual, tabular, or graphical presentation formats, for displaying to a system user. The presentation of the output information may include audio or other media format to alert the system user of the detected physiological events.

In some examples, the arrhythmia detection system 200 may additionally include a therapy circuit 260 that is configured to deliver a therapy to the patient in response to the detection of the arrhythmia. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 260 may modify an existing therapy, such as adjust a stimulation parameter or drug dosage.

Although the example as illustrated in FIG. 2 may be used for detecting cardiac arrhythmias, in some examples, at least a portion of the arrhythmia detector circuit 230 may be modified and configured to detect various physiologic events other than cardiac arrhythmias, including progression of a chronic disease, such as a worsening heart failure, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

Figure 3:
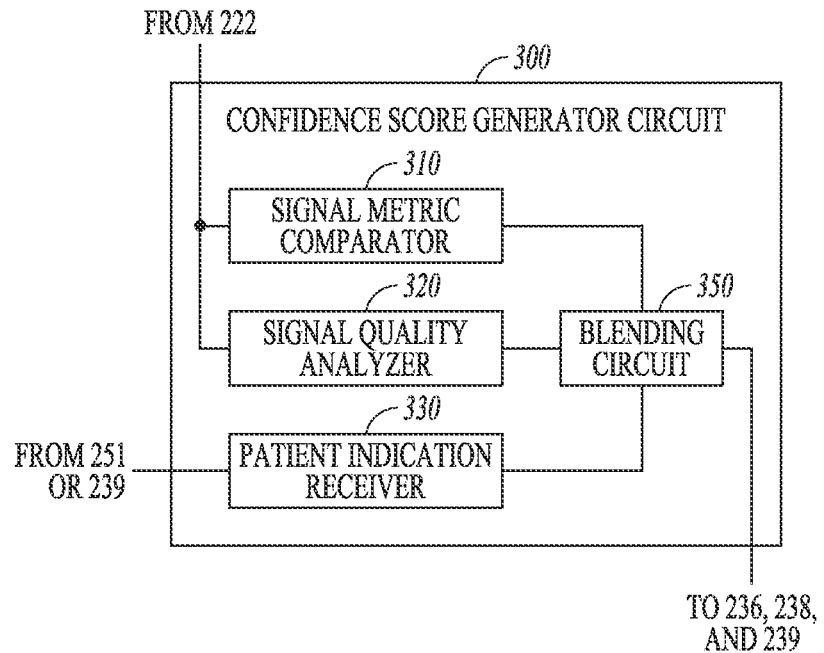
FIG. 3 illustrates generally an example of a circuit for generating a confidence score associated with a detection of cardiac arrhythmic event.

FIG. 3 illustrates generally an example of a confidence score generator circuit 300 for generating a confidence score associated with a detection of cardiac arrhythmic event. The confidence score generator circuit 300 may be an embodiment of the confidence indicator generator 234 of FIG. 2, and may be implemented in an IMD 110, or as a part of the external system 120. The confidence score generator circuit 300 may include one or more of a signal metric comparator 310, a signal quality analyzer 320, a patient indication receiver 330, and a blending circuit 350.

The signal metric comparator 310 may compare the signal metric 222 to one or more thresholds, and generate a confidence score associated with the arrhythmia detection. The confidence score may be proportional to a deviation of the signal metric 222 from a reference value such as the detection threshold used for detecting the cardia arrhythmic event. In an example, the first arrhythmia detector 232 may generate a beat ratio (R) of the number of unstable beats ($N_U$) to the sum of numbers of stable and unstable beats, that is, $R=N_U/(N_S+N_U)$. If the beat ratio exceeds a beat ratio threshold $R_{TH}$ (that is $R>R_{TH}$), then an AF event is deemed detected. The first arrhythmia detector 232 may determine a confidence score ($C_1$) associated with the arrhythmia detection as $C_1=f_1(R-R_{TH})$. In an example, the first arrhythmia detector 232 computes a morphological similarity score S between a template and morphology measurements of the signal metric, and detects the arrhythmic event if S exceeds the similarity threshold $S_{TH}$. The first arrhythmia detector 232 may determine a confidence score ($C_2$) associated with the arrhythmia detection as $C_2=f_2(S-S_{TH})$. The functions $f_1$ and $f_2$ may each be a growth function, such as a linear growth, exponential growth, or other types of growth function. In an example, the first arrhythmia detector 232 may detect an AF event using both beat ratio R and morphological similarity S. The blending circuit 350 may combine the confidence scores associated with the detected arrhythmic event, such as using a linear function $C=k_1C_1+k_2C_2$ where $k_1$ and $k_2$ are scaling factors. Alternatively, the blending circuit 350 may include a multivariate function (g) of at least both the beat counts deviation ($R-R_{TH}$) and the similarity score deviation ($S-S_{TH}$), that is, $C=g(R-R_{TH}, S-S_{TH})$. The confidence score C may also be proportional to statistical or morphological differences between a non-arrhythmic event and a sinus rhythm. In some examples, two or more signal metrics extracted from one or more physiological signals may be used for detecting cardia arrhythmias and for generating respective confidence scores. The blending circuit 350 may generate a composite confidence score using a linear or nonlinear combination of deviations of two or more signal metrics from respective detection thresholds.

The signal quality analyzer 320 may determine a signal quality indicator from the signal metrics 222, or the physiological signal from which the signal metrics 222 are generated, and generate a confidence score proportional to the signal quality. Examples of the signal quality indictor may include a signal-to-noise ratio (SNR), a detection of motion artifact, or a detection of ectopic beats such as premature atrial contractions (PACs) or premature ventricular contractions (PVCs). An indicator of low signal quality may be generated if the ectopic beat count within a specified time period exceeds a threshold, or the degree of motion artifact exceeds a specified noise floor, or the SNR falls below a threshold value. The signal quality analyzer 310 may generate a confidence score proportional to the deviation of the SNR, motion artifact level, or the ectopic beat counts from their respective reference values such as respective thresholds. In an example, the blending circuit 350 may generate a composite confidence score using a linear or nonlinear combination of deviations of various signal quality indicators from respective thresholds.

The patient indication receiver 330 may receive from the user input module 151 a user input, or from the memory circuit 239 stored information, of patient medical history. The patient medical history includes information relevant to patient risk of developing an arrhythmic event, or the responsiveness of a physiological sensor to an arrhythmic event. Examples of the medical history may include a history of syncope, an arrhythmia history, a medical procedure such as an ablation procedure, or a duration of a prior arrhythmic event, among others. For example, in determining the confidence score associated with a detected AF event, the confidence score may be decreased if the patient had a previous syncope episode, while the confidence score may be increased if the patient had a previous AF ablation procedure. If AF episodes with short durations have been frequently detected within a specified timeframe, the presently detected AF even is more likely a continuation of the underlying sustained AF rhythm and a higher confidence score may be assigned accordingly.

The blending circuit 350, in addition to combining confidences generated from different signal metrics or with different information sources within each of 310-330, may also combine factors affecting confidence of the arrhythmia detection from two or more of 310-330, and generate a composite confidence score for use in determining whether to confirm the detected arrhythmia at the second arrhythmia detector 236, or to generate the alert at the alert generator 238, or to store the detected arrhythmic events at the memory circuit 239.

Figure 4:
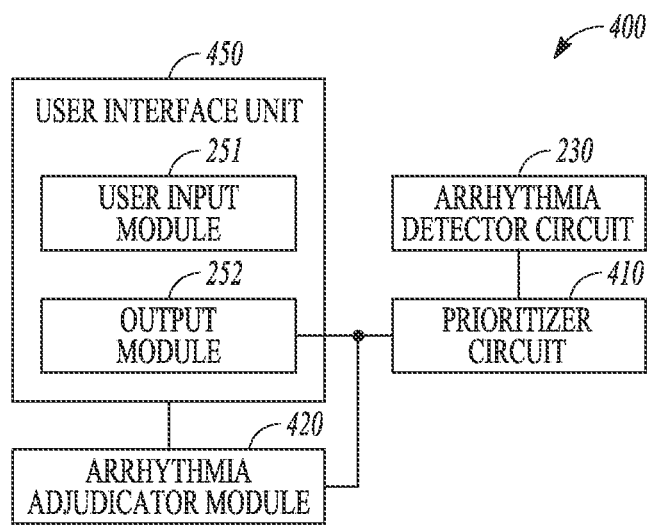
FIG. 4 illustrates generally an example of a portion of an arrhythmia detection and prioritization system.

FIG. 4 illustrates generally an example of a portion of an arrhythmia detection and prioritization system 400. The system 400 may be an embodiment of the arrhythmia detection system 200. The system 400 may include the arrhythmia detector circuit 230 to detect and confirm two or more arrhythmic events. The two or more confirmed arrhythmic events and their respective confidence scores may be stored in the memory circuit 239. The system 400 may include a prioritizer circuit 410 coupled to the arrhythmia detector circuit 230. The prioritizer circuit 410 may include a comparator circuit to prioritize the two or more detected arrhythmic events in an order based on the respective confidence scores, such as an ascending order or a descending order of the confidence scores. The prioritized arrhythmic events, optionally along with their respective confidence scores, may be presented to the clinician at the output module 252. The prioritizer circuit 410 and the arrhythmia adjudicator module 420 may include hardware, software, or firmware communicatively coupled to one or more processors in order to carry out the operations described herein. In an example, the prioritizer circuit 410 or the arrhythmia adjudicator module 420 may be implemented as a part of a microprocessor circuit. Portions of the prioritizer circuit 410 or the arrhythmia adjudicator module 420 may be implemented in the IMD 110, in the external system 120, or distributed between the IMD 110 and the external system 120.

In an example, the prioritized arrhythmic events may be transmitted to an arrhythmia adjudicator module 420 that enables a clinician to provide adjudication input about the detected arrhythmic events. The adjudication input may include affirming, overriding, revising, or otherwise editing the detected arrhythmic events. In an example, the prioritizer circuit 410 may be configured, such as by the controller circuit 240, to present a portion of the detected arrhythmic events to the arrhythmia adjudicator module 420 for adjudication. For example, only those detected arrhythmic events having confidence scores below a specified confidence threshold or within a specified range thus indicative of a relative low confidence of detection are presented to the arrhythmia adjudicator module 420. In an example, the arrhythmia adjudicator module 420 may be implemented as a part of the user interface unit 450, and coupled to the user input module 251 and the output module 252 to enable a user such as a clinician to interactively adjudicate the detected arrhythmic events as presented on the output module 420.

Figure 5:
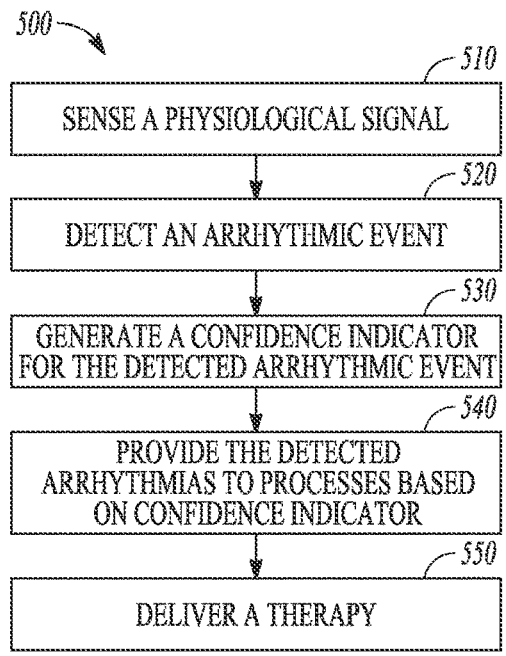
FIG. 5 illustrates generally an example of a method for detecting a target cardiac arrhythmia from a patient.

FIG. 5 illustrates generally an example of a method 500 for detecting a target cardiac arrhythmia from a patient. Examples of cardiac arrhythmias may include atrial fibrillation (AF), atrial flutter (AFL), atrial tachycardia, paroxysmal supraventricular tachycardia (PSVT), Wolff-Parkinson-White (WPW) syndrome, ventricular tachycardia, ventricular fibrillation, bradycardia, or sinus pauses, among others. The method 500 may be implemented and operate in an ambulatory medical device such as an implantable or wearable medical device, or in a remote patient management system. In an example, the method 500 may be performed by the confidence-based arrhythmia detector 113 or any embodiment thereof, or by the external system 120.

The method 500 begins at 510 by sensing a physiological signal from a patient. Examples of the physiological signals may include surface electrocardiography (ECG) such as sensed from electrodes on the body surface, subcutaneous ECG such as sensed from electrodes placed under the skin, intracardiac electrogram (EGM) sensed from the one or more electrodes of the leads 108A-C or the can housing 112, heart rate signal, heart rate variability signal, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others.

The sensed physiological signal may be pre-processed, including one or more of signal amplification, digitization, filtering, or other signal conditioning operations. In an example, a plurality of heart beats may be detected from a cardiac electrical signal or a cardiac mechanical signal. One or more statistical or morphological signal metrics may be extracted from the pre-processed signal. The signal metrics may include timing parameters, or statistical or morphological parameters associated with the beats detected from the sensed physiological signal.

At 520, an arrhythmic event may be detected from the signal metrics, such as by using the arrhythmia detector circuit 230 as illustrated in FIG. 2. The arrhythmia detection may be based on timing information or morphology measurements from the signal metrics. In an example, based on the variability of the CI or the HR associated with the detected beats, the detected heart beats may be classified into one of a plurality of beat classes including a stable beat class, an unstable beat class, and a random beat class. The beat counts of each beat class within a specified time period may be determined, and a relative quantity such as a ratio of the number of unstable beats to a sum of the numbers of the stable and unstable beats, or a ratio of the number of random beats to a sum of the numbers of the stable and unstable beats, may be computed. An arrhythmic event, such as an AF event, may be detected if the relative quantity exceeds a detection threshold. In another example, a heart rate distribution may be generated using a plurality of heart rates within a specified time period, and a parameter extracted from the heart rate distribution may be used for detecting the arrhythmic event such an AF event. Examples of the distribution parameter may include a central tendency (e.g., a mode) of heart rates within the specified time period, or a relative number (e.g., a percentage) of the heart beats falling within a specified margin of the central tendency of the heart rates. An arrhythmic event, such as an AF event, may be detected if the central tendency of the heart rates, or the relative number of the heart beats within the margin of the central tendency satisfies a specified condition. In yet another example, morphology measurements may be extracted from a plurality of heart beats and compared to a morphology template of a known cardia rhythm such as normal sinus rhythm or AF. An arrhythmic event, such as an AF event, may be detected if a similarity score between the template and the morphology measurements of the signal metrics satisfies a specified condition, such as when the difference falls below a specified detection threshold.

At 530, a confidence indicator may be generated for the detected arrhythmic event. The confidence indicator may have a categorical value or a numerical value. A numerical confidence score may be computed based on a comparison of the signal metrics and one or more thresholds. In an example, the confidence score may be proportional to deviations of the one or more signal metrics from respective reference values such as respective detection thresholds. As previously discussed with reference to FIG. 3, the confidence score associated with the detected AF event may be a linear or non-linear growth function of the beat ratio (R) (such as a ratio of the number of unstable beats to the sum of numbers of stable and unstable beats) and a beat ratio threshold $R_{TH}$, or a morphology similarity (S) (such as a correlation or a distance between a template and morphology measurements of the signal metric) and a threshold Sm. In an example, the confidence indicator may be a composite confidence score computed as a linear or nonlinear combination of deviations of two or more signal metrics from respective thresholds. In some examples, the confidence indicator may be adjusted based on additional information including a signal quality of the signal metric or a medical history of the patient. Examples of the signal quality may include one of a signal-to-noise ratio, a detection of motion artifact, or a detection of ectopic beats such as premature atrial contractions (PACs) or premature ventricular contractions (PVCs). In an example, the confidence score may be proportional to the deviation of the SNR, motion artifact level, or the ectopic beat counts from their respective thresholds. Examples of the medical history may include one of a history of syncope, an arrhythmia history, an ablation procedure, or a duration of a prior arrhythmic event. In an example, the confidence score may be decreased if the patient had a previous syncope episode, while the confidence score may be increased if the patient had a previous AF ablation procedure.

At 540, the detected arrhythmias may be provided to different processes based on confidence indicator. If the confidence indicator indicates a high confidence of arrhythmia being detected, the detected arrhythmic event may be provided to a first process, such as for generating an alert to a healthcare professional of the detected arrhythmic event. If the confidence indicator indicates a low confidence associated with the detected arrhythmia, the detected arrhythmic event may be provided to at least a second process different from the first process, such as a reconfirmation of the detected arrhythmic event using a different detection process. A human-perceptible presentation of information, including one or more of the detection of the target cardiac arrhythmia, confidence indicators associated with the detected arrhythmic events, or alerts about the detected arrhythmias may be generated and presented to a clinician such as via the user interface 250 as illustrated in FIG. 2.

In some examples, as illustrated in FIG. 5, the method 500 may additionally include a step 550 of delivering a therapy to the patient in response to the detection of the arrhythmia. Examples of the therapy may include electrostimulation therapy delivered to the heart, a nerve tissue, other target tissues, a cardioversion therapy, a defibrillation therapy, or drug therapy including delivering drug to a tissue or organ. In some examples, at 550, an existing therapy may be modified to treat the detected arrhythmia, such as adjust a stimulation parameter or drug dosage.

Figure 6:
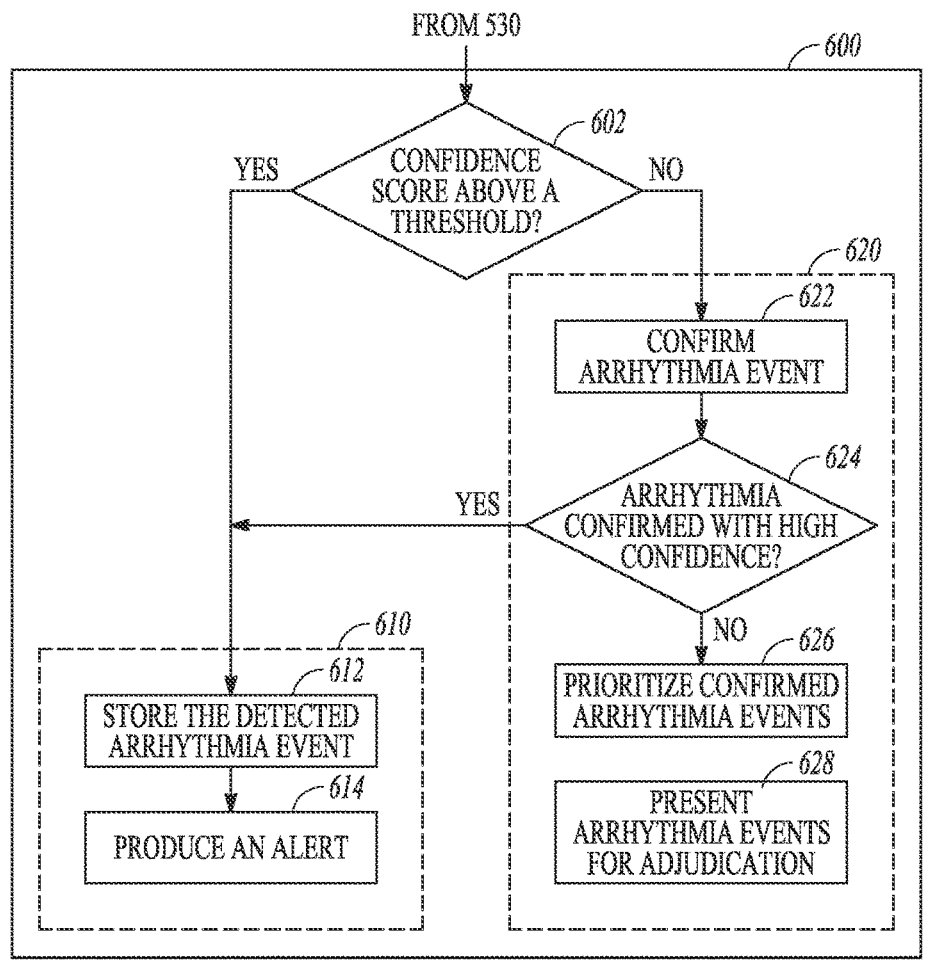
FIG. 6 illustrates generally an example of a method for providing the detected arrhythmic events for further processing based on the confidence indicator associated with the detected arrhythmic events.

FIG. 6 illustrates generally an example of a method 600 for providing the detected arrhythmic events for further processing based on the confidence indicator associated with the detected arrhythmic events. The method 600 may be an embodiment of the step 540 of the method 500. In an example, the method 600 may be implemented in and executed by the arrhythmia detection system 200 in FIG. 2, or the arrhythmia detection and prioritization system 400 in FIG. 4.

At 602, the confidence score such as generated at 530 in FIG. 5 may be compared to a confidence threshold which may be pre-determined or editable by a user. If the confidence score exceeds the confidence threshold, a high confidence of the detected arrhythmic event is indicated. The detected arrhythmic event, and optionally the corresponding confidence score, may be provided to a first process 610. The first process 610 may include storing the detected arrhythmic event (such as the physiological data during the detected arrhythmia) in a memory at 612. In an example, as previously discussed with reference to FIG. 2, the amount of date stored may be based on the confidence score, such that a shorter duration of the physiological data is stored for the detected arrhythmic event with higher confidence, and longer duration of the physiological data is stored for the detected arrhythmic event with lower confidence. The first process 610 may alternatively or additionally include producing an alert to a clinician of the detected arrhythmic event at 614. The alert may be accompanied by a report presenting to the clinician, which may include information such as arrhythmic event detection, confidence indicators associated with the detected arrhythmic events, or other system information.

If at 602 the confidence score does not exceed the confidence threshold, a low confidence of the detected arrhythmic event is indicated. The detected arrhythmic event, and optionally the corresponding confidence score, may be provided to a second process 620. The second process 620 may include confirming the detected arrhythmic event at 622, such as by using the second arrhythmia detector 236 or additional arrhythmia detectors. The confirmation of the detected arrhythmic event may include retrospective analysis of historical physiological data collected from the patient, such as using a more computationally intensive arrhythmia detection algorithm or data from additional physiological sensors. If the arrhythmic event is confirmed, then at 624 a confidence score may be determined for the reconfirmed arrhythmic event. In an example, the confidence score used at 624 may be the confidence score associated with the initial detection, as determined at 530. In another example, the confidence score used at 624 may be generated using at least the arrhythmia confirmation result at 622, such that the confidence score is proportional to a deviation of a signal metric used by the second arrhythmia detector 236 from a corresponding threshold. The resulting confidence score thus computed may be different from the confidence score associated with the initial detection as determined at 530.

If the confidence score exceeds the confidence threshold at 624, a high confidence of the confirmed arrhythmic event is indicated. The confirmed arrhythmic event, and optionally the corresponding confidence score, may be provided to the first process 610, where the confirmed arrhythmic event may be stored, or an alert and optionally a report may be generated and presented to a clinician. However, if at 624 the arrhythmic event is not confirmed (such as the second arrhythmia detector 236 does not detect the same arrhythmic event that has been detected by the first arrhythmic detector 232, or if the confidence score falls below the confidence threshold), then at 626 the detected arrhythmic events may be prioritized in an order based on the respective confidence scores, such as an ascending order or a descending order of the confidence scores. At 628, the prioritized arrhythmic events, or a selected portion of the prioritized arrhythmic events such as those with confidence scores below a specified threshold, may be presented to a clinician for arrhythmia review or adjudication. The adjudication process may be performed via the arrhythmia adjudicator module 420 which enables a clinician to provide classification input about the detected arrhythmic events, including affirming, overriding, revising, or otherwise editing the detected arrhythmic events.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system, comprising:
a physiological sensor circuit configured to receive physiological information including a physiological signal sensed from a subject;
a first arrhythmia detector circuit configured to detect arrhythmic events each comprising a plurality of heart beats and indicating at least a presence or an absence of cardiac arrhythmia using the received physiological information;
a confidence indicator generator circuit configured to:
generate respective confidence scores for the detected arrhythmic events by the first arrhythmia detector circuit, the confidence scores indicating levels of confidence of the presence of the cardiac arrhythmia in the respective detected arrhythmic events, the confidence scores including at least a high confidence score and a low confidence score, the low confidence score lower than the high confidence score; and identify, from the detected arrhythmic events by the first arrhythmia detector circuit, a first set of arrhythmic events with respective confidence scores below a confidence threshold, and a second set of arrhythmia events with respective confidence scores above the confidence threshold;

a second arrhythmia detector circuit configured to confirm or reject only the first set of the arrhythmic events but not the second set of the arrhythmic events detected by the first arrhythmia detector circuit;

wherein the confidence indicator generator circuit is configured to generate respective confirmatory confidence scores of the confirmed respective detected arrhythmic events of the second arrhythmia detector circuit;

a prioritizer circuit configured to determine respective priorities of the detected arrhythmic events based on the respective confidence scores and the respective confirmatory confidence scores; and an output circuit configured to prioritize display of at least a portion of the received physiological signal corresponding to at least one of the detected arrhythmic events according to the determined priorities.

2. The system of claim 1, comprising a controller circuit configured to:
store the respective detected arrhythmic events of the first arrhythmia detector circuit having the high confidence score in a memory circuit; and
produce an alert signal.

3. The system of claim 1, wherein:
the physiological sensor circuit is configured to receive the physiological information including a cardiac signal; and
the first arrhythmia detector circuit includes a filter circuit to generate a signal metric from the cardiac signal, the first arrhythmia detector circuit configured to detect the arrhythmic events in response to the signal metric satisfying a specified condition, the arrhythmic events including an atrial or ventricular arrhythmia event.

4. The system of claim 3, wherein the signal metric includes morphology measurements of a plurality of heart beats from the cardiac signal, and wherein the first arrhythmia detector circuit is to detect an arrhythmic event using the morphology measurements of the plurality of heart beats.

5. The system of claim 3, wherein the confidence indicator generator circuit is to determine a confidence score of a detected arrhythmic event to be proportional to a deviation of the signal metric from a reference value.

6. The system of claim 5, wherein the confidence indicator generator circuit is to determine the confidence score using a combination of deviations of two or more signal metrics from respective reference values.

7. The system of claim 6, wherein the confidence indicator generator circuit is to:
determine a beat ratio of a count of unstable beats to a count of total beats in the cardiac signal;
determine a morphological similarity score between (i) morphology measurements of the plurality of heart beats in the cardiac signal and (ii) a beat morphology template; and
determine the confidence score using a combination of (i) a first deviation of the determined beat ratio from a beat ratio threshold, and (ii) a second deviation of the determined morphological similarity score from a similarity threshold.

8. The system of claim 3, wherein the confidence indicator generator circuit is to determine a confidence score of a detected arrhythmic event based on at least one of a signal quality of the signal metric or a medical history of the subject,
wherein the signal quality includes one of a signal-to-noise ratio, a detection of motion artifact, or a detection of ectopic beats; and
wherein the medical history includes one of a history of syncope, an arrhythmia history, an ablation procedure, or a duration of a prior arrhythmic event.

9. The system of claim 1,
wherein the output circuit is configured to present to a user the at least a portion of the received physiologic information corresponding to first one or more of the detected arrhythmic events having respective first confidence scores, and to withhold presenting to the user the at least a portion of the received physiologic information corresponding to second one or more of the detected arrhythmic events having respective second confidence scores higher than the first confidence scores, and
wherein the at least a portion of the received physiologic information corresponding to at least one of the prioritized arrhythmic events comprises at least a portion of a physiologic signal corresponding to the prioritized arrhythmic event.

10. The system of claim 1, further comprising a first implantable device including the first arrhythmia detector circuit and a different second device including the second arrhythmia detector circuit,
wherein the second arrhythmia detector circuit is configured to confirm or reject the respective detected arrhythmic events having the low confidence score using a more computationally intensive algorithm having a higher sensitivity or specificity than the first arrhythmia detector circuit.

11. The system of claim 1, wherein:
the first arrhythmia detector circuit is configured to detect an arrhythmic event using first physiological information received from the subject; and
the second arrhythmia detector circuit is configured to confirm or reject the respective detected arrhythmic events having the low confidence score using second physiological information received from the subject, the second physiological information being different from the first physiological information.

12. The system of claim 1, wherein the confirmatory confidence scores include at least a high confirmatory confidence score and a low confirmatory confidence score, the low confirmatory confidence score lower than the high confirmatory confidence score, the system further comprising a controller circuit configured to:
store the respective detected arrhythmic events of the second arrhythmia detector circuit having the high confirmatory confidence scores in a memory circuit and produce an alert signal; and
present the respective detected arrhythmic events of the second arrhythmia detector circuit having the low confirmatory confidence scores to a user.

13. A method for detecting an arrhythmic event via a medical system, the method comprising:
receiving, via a physiological sensor circuit, physiological information including a physiological signal sensed from a subject;
detecting, via a first arrhythmia detector circuit, arrhythmic events each comprising a plurality of heart beats and indicating at least a presence or an absence of cardiac arrhythmia using the received physiological information;

generating, via a confidence indicator generator circuit, respective confidence scores for the detected arrhythmic events by the first arrhythmia detector circuit, the confidence scores indicating levels of confidence of the presence of the cardiac arrhythmia in the respective detected arrhythmic events, the confidence scores including at least a high confidence score and a low confidence score, the low confidence score lower than the high confidence score;

identifying, from the detected arrhythmic events by the first arrhythmia detector circuit, a first set of arrhythmic events with respective confidence scores below a confidence threshold, and a second set of arrhythmia events with respective confidence scores above the confidence threshold;

confirming or rejecting, via a second arrhythmia detector circuit different from the first arrhythmia detector circuit, only the first set of the arrhythmic events but not the second set of the arrhythmic events detected by the first arrhythmia detector circuit;

generating respective confirmatory confidence scores of the confirmed respective detected arrhythmic events of the second arrhythmia detector circuit;

determining, via a prioritizer circuit, respective priorities of the detected arrhythmic events based on the respective confidence scores and the respective confirmatory confidence scores; and prioritizing display of, via an output circuit, at least a portion of the received physiological signal corresponding to at least one of the prioritized arrhythmic events according to the determined priorities.

14. The method of claim 13, further comprising generating one or more signal metrics from a cardiac signal, wherein detecting the arrhythmic events includes detecting an atrial or ventricular arrhythmia using the one or more signal metrics.

15. The method of claim 14, wherein the one or more signal metrics include morphology measurements of a plurality of heart beats from the cardiac signal, and wherein detecting the arrhythmic events is based on the morphology measurements of the plurality of heart beats.

16. The method of claim 14, wherein a confidence score of a detected arrhythmic event is proportional to deviations of the one or more signal metrics from respective reference values.

17. The method of claim 14, wherein a confidence score of a detected arrhythmic event is generated based on one of a signal quality of the signal metric or a medical history of the subject,
wherein the signal quality includes one of a signal-to-noise ratio, a detection of motion artifact, or a detection of ectopic beats; and
wherein the medical history includes one of a history of syncope, an arrhythmia history, an ablation procedure, or a duration of a prior arrhythmic event.

18. The method of claim 13, comprising:
storing the respective detected arrhythmic events of the first arrhythmia detector circuit having the high confidence score in a memory circuit; and
producing an alert signal.

19. The method of claim 13, further comprising:
via the output circuit, presenting to a user first one or more of the detected arrhythmic events having respective first confidence scores, and withholding presenting to the user second one or more of the detected arrhythmic events having respective second confidence scores higher than the first confidence scores; and
receiving from the user, via a user interface, adjudication of the first one or more of the detected arrhythmic events.

20. The method of claim 13, wherein:
detecting the arrhythmic events includes using first physiological information received from the subject; and
confirming or rejecting the respective detected arrhythmic events having the low confidence score includes using second physiological information received from the subject, the second physiological information being different from the first physiological information.

* * * * *